United States Patent

Smith

(10) Patent No.: US 6,955,093 B2
(45) Date of Patent: Oct. 18, 2005

(54) RUPTURE TESTING FOR GLOVES

(75) Inventor: Scott Carl Smith, Reno, NV (US)

(73) Assignee: Microflex Corporation, Reno, NV (US)

( * ) Notice: Subject to any disclaimer, the term of this patent is extended or adjusted under 35 U.S.C. 154(b) by 259 days.

(21) Appl. No.: 09/977,370

(22) Filed: Oct. 16, 2001

(65) Prior Publication Data

US 2003/0074979 A1 Apr. 24, 2003

(51) Int. Cl.$^7$ .................................................. G01N 3/08
(52) U.S. Cl. ......................................................... 73/830
(58) Field of Search ........................ 73/830, 783, 788, 73/790, 799, 81

(56) References Cited

U.S. PATENT DOCUMENTS

| | | |
|---|---|---|
| 2,748,596 A | 6/1956 | Tasker |
| 3,315,519 A | 4/1967 | Ferguson |
| 4,055,071 A | 10/1977 | Frazier |
| 4,136,557 A | 1/1979 | Bell, Jr. et al. |
| 4,206,631 A | 6/1980 | Nysse et al. |
| 4,699,000 A | 10/1987 | Lashmore et al. |
| 4,856,326 A | 8/1989 | Tsukamoto |
| 4,860,589 A | 8/1989 | Williford |
| 4,930,355 A | 6/1990 | Heck |
| 5,129,256 A | 7/1992 | McGlothlin |
| 5,493,899 A | 2/1996 | Beck et al. |
| 5,507,189 A | 4/1996 | Kim et al. |
| 6,339,958 B1 * | 1/2002 | Tsui et al. ................. 73/290 R |
| 6,401,349 B1 * | 6/2002 | Onyon ........................ 33/551 |

* cited by examiner

*Primary Examiner*—Michael Cygan
*Assistant Examiner*—Andre Allen
(74) *Attorney, Agent, or Firm*—Evan M. Kent; Stewart L. Gitler; Christopher J. McDonald

(57) ABSTRACT

An apparatus for measuring the penetration depth of a blunt object before failure of a film sample, such as a glove. Failure occurs when a film sample secured to a column ruptures from the force applied by a stylus. The penetration depth of the blunt object is equal to the distance traveled by the stylus under the method of the invention. With the measurement of the penetration depth and the force applied by the stylus, a quantitative measurement of the rupture strength of the film sample is obtained.

17 Claims, 2 Drawing Sheets

RUPTURE TESTING FOR GLOVES

BACKGROUND OF THE INVENTION

The invention relates to a methodology for testing the rupture strength of surgical gloves.

Gloves are used to insure a sanitary environment, particularly in the medical profession. The use of gloves prevents communicable diseases from spreading between a patient and a health care provider. It is important that the gloves do not rip or rupture since such an event renders the gloves useless. For purposes of product development and quality assurance, the penetration depth by a blunt object before failure and rupture strength of the gloves must be known with some degree of certainty. A test for determining the penetration depth by a blunt object and rupture strength of a glove should be easy to conduct and provide accurate results.

It is necessary to have a test for measuring the penetration depth of a blunt object of a film sample at failure.

It is also necessary to have a test that reliably and quantitatively measures the rupture strength of gloves.

It is an object of the invention to provide a simple accurate means for testing the penetration depth of a blunt object at failure for film samples such as gloves.

It is another object of the invention to measure the penetration depth and force applied to a film sample at failure to calculate the rupture strength.

It is yet another object of the invention to provide a test for the penetration depth of a blunt object that is easy to administer.

It is yet another object of the invention to provide an apparatus for testing latex film that is reliable and inexpensive to use.

These and other objects of the invention will become apparent after reading the disclosure of the invention.

SUMMARY OF THE INVENTION

An apparatus for measuring the penetration depth of a blunt object before failure of a film sample, such as a glove. Failure occurs when a film sample secured to a column ruptures from the force applied by a stylus. The penetration depth of the blunt object is equal to the distance traveled by the stylus under the method of the invention. With the measurement of the penetration depth and the force applied by the stylus, a quantitative measurement of the rupture strength of the film sample is obtained.

DETAILED DESCRIPTION OF THE INVENTION

Figure 2:
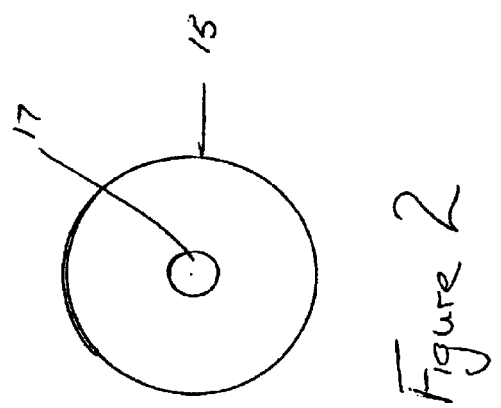
FIG. 2 is a top view of the column of the apparatus.
Figure 1:
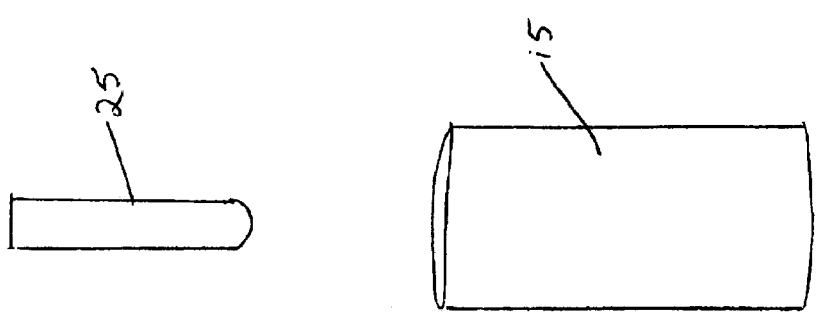
FIG. 1 is a side view of the column and stylus of the apparatus.

The apparatus for testing the rupture strength of a sample from a glove is depicted in FIG. 1. The device uses a column 15 for holding the sample and a stylus 25 for applying force to the sample. The cylindrical column measures at least 160 mm and is fastened to a non-movable base. In the preferred embodiment, the opening of the column has a diameter of 30 mm. The column is placed beneath a moving carriage which holds a projectile stylus having a blunt end. The stylus is the object that ruptures the sample and in the preferred embodiment has a diameter of at least 7 mm and a length greater than the column. The stylus is connected to the movable carriage by a connection similar to a drill bit socket. The socket is preferably adjustable to hold styluses of different diameters. FIG. 2 shows a top view of the column 15 where a hole 17 in the bottom of the column is seen. The hole is approximately 1 cm in diameter and is necessary for vacuum protection.

Figure 3:
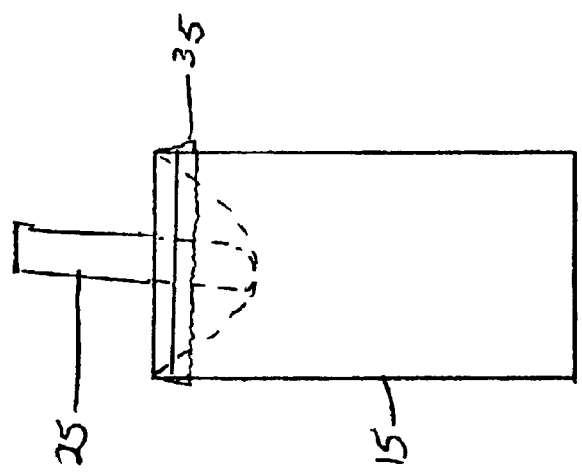
FIG. 3 is a view of the device in use.

Any part of a latex or natural rubber latex (NRL) film or glove can be used as a sample. The section of glove used has an effect on the set-up and testing which is depicted in FIG. 3. For testing the finger portion of a glove, a finger is cut from the glove at or just above the palm-finger intersection. The cut section 35 is then extended over a column creating a nipple. The finger is fastened to the outside of the column with fine wire 19 and the distance from the base of the nipple to the top of the column is regulated to be consistent.

The stylus 25, secured to the movable carriage, is then positioned at the base of the nipple. The base is the closest region to the bottom of the column. The stylus is positioned so as not to apply any tension to the nipple, but is positioned so that upon movement of the carriage, there is movement of the nipple. The stylus and sample portion inside the column are shown in phantom in FIG. 3.

When testing a section of a glove palm or uniform thickness film, the sample is extended over the column's opening. The sample is fastened first with a rubber band and then securely fastened with a fine wire. The film should be applied so as not to be taut over the opening, so there should be some slack. The stylus, again attached to the movable carriage, is positioned at the center of the sample and positioned on the sample so that the previously loose sample is now taut, but not stressed. Similar to the set-up for a finger portion, there should be no movement of the stylus without movement of the sample. This set-up procedure is also used when a portion of the glove cuff is to be tested.

After the sample to be tested has been secured to the column and the stylus correctly positioned, the sample is tested. By testing, the stylus is moved downwardly into the column until the sample ruptures. During testing, the projectile moves at a consistent speed of 508.00 mm/min. After the sample has been ruptured, measurements and calculations are made. The distance traveled by the stylus between the starting point and the point of failure is measured. This is the penetration depth of a blunt object for the sample. It is referred to as the extension, and measured in millimeters. The load is measured in Newtons and is the amount of force applied to the sample by the stylus at rupture. Also, the thickness of the sample is measured as the average single wall thickness of the sample. This is also measured in millimeters. From these two measurements, the rupture strength/ resistance is calculated. This is calculated by the load, in Newtons normalized by the single wall thickness, in millimeters, by the following formula:

$$\text{Load/Thickness (N/mm)}$$

A reporting of only the force applied has been shown to be an incomplete representation of the glove sample performance. It is important that the stylus travel distance be incorporated into calculations. In order to incorporate force, thickness and stylus travel distance in a reportable manner, the following equation has been adopted:

$$((0.5)*(\text{Stylus Travel Distance(mm)})*(\text{Normalized Load N/mm}))$$

If the normalized load, measured in Newtons per millimeter is plotted on a graph's Y axis and the stylus travel distance on the X axis, the utilized equation calculates the area of a representative triangle. Taking the area of the triangle approximates an integral. This approximation offers a quantitative value representative of both the force normalized by thickness and projectile travel thickness.

Altering the dimensions of the apparatus, such as the diameter of the column and the stylus would have an effect on the test results. Therefore, it is critical that all samples be tested on uniform equipment. If the diameter of the stylus is increased, a increase in the applied force results and the distance traveled by the stylus is decreased. Conversely, if the diameter of the stylus is decreased, a decrease in the force applied results and there is a resulted increase in the distance traveled by the stylus before rupture. The length of the column allows for a potentially longer distance for the stylus to travel before rupture. Therefore, the length of the column must be chosen so that the stylus can travel as far as necessary to achieve rupture. The dimensions of the stylus and column can be changed, but it is important that when comparing results between different tests, the dimensions of the apparatus be uniform. Since changing the dimensions would have an effect on the results, only results from identical apparatuses can be compared with one another.

The following chart indicates results from tests conducted with the disclosed method and the resulting calculation.

CUFF RUPTURE

|   | Max Load (N) | Load/Thickness (N/mm) | Mean Extension (mm) |
|---|---|---|---|
| 1 | 20.844 | 157.91 | |
| 2 | 21.591 | 163.57 | |
| 3 | 20.124 | 152.45 | |
| 4 | 22.263 | 168.66 | |
| 5 | 24.946 | 188.98 | |
| Mean | 21.954 | 166.32 | 88.49 |
| S.D. | 1.854744807 | 14.05 | 4.09 |
| Thickness | 0.132 | | |

Rupture Resistance (.05 * Extension * (Load/Thickness)) 7358.61

PALM RUPTURE

|   | Max Load (N) | Load/Thickness (N/mm) | Mean Extension (mm) |
|---|---|---|---|
| 1 | 37.738 | 216.89 | |
| 2 | 28.899 | 166.09 | |
| 3 | 25.759 | 148.04 | |
| 4 | 26.573 | 152.72 | |
| 5 | 26.742 | 153.69 | |
| Mean | 29.142 | 167.48 | 93.45 |
| S.D. | 4.943549201 | 28.41 | 7.1 |
| Thickness | 0.174 | | |

Rupture Resistance (.05 * Extension * (Load/Thickness)) 7825.69

TIP RUPTURE

|   | Max Load (N) | Load/Thickness (N/mm) | Mean Extension (mm) |
|---|---|---|---|
| 1 | 44.031 | 205.75 | |
| 2 | 49.555 | 231.57 | |
| 3 | 43.43 | 202.94 | |
| 4 | 43.428 | 202.93 | |
| 5 | 32.844 | 153.48 | |
| Mean | 42.658 | 199.33 | 132.6 |
| S.D. | 6.061295596 | 28.32 | 9.59 |
| Thickness | 0.214 | | |

Rupture Resistance (.05 * Extension * (Load/Thickness)) 13215.88

While the invention has been described with reference to a preferred embodiment, variations and modifications would be apparent to one of ordinary skill in the art without departing from the scope of the invention. The method and apparatus of the invention have been described with reference to particular dimensions of the stylus and column, but other dimensions could be used without departing from the scope of the invention. The invention encompasses such variations and modifications and is defined by the appended claims.

What is claimed is:

1. A method for testing a film sample, comprising:
   securing the sample to the top end of a column,
   forming an aperture in the bottom of said column for vacuum protecting,
   lowering a stylus to contact the sample until movement of the stylus is not possible without movement of the sample,
   recording a vertical height of the stylus,
   moving the stylus downward until the sample ruptures,
   measuring the distance traveled by the stylus from the starting point and the rupture point, and
   measuring the force applied by the force applied by the stylus at rupture.

2. The method of claim 1, wherein the stylus is lowered at a constant speed.

3. The method of claim 2, wherein said constant speed is 508.0 mm/min.

4. The method of claim 1, wherein the sample is a glove finger.

5. The method of claim 1, wherein the sample is taken from a glove palm or glove cuff.

6. The method of claim 1, wherein the sample is a uniform thickness film.

7. The method of claim 1, further comprising calculating the rupture strength of the sample by using the formula:

$$(0.5) * \left(\begin{array}{c}\text{Stylus Travel Distance}\\ \text{at Rupture}\end{array}\right) * \left(\begin{array}{c}\text{Stylus Force}\\ \text{at Rupture}\end{array} \Big/ \begin{array}{c}\text{Sample}\\ \text{Thickness}\end{array}\right).$$

8. The method of claim 1, wherein said stylus is longer than said column.

9. The method of claim 1, wherein said column has a diameter of 30 mm and said stylus has a diameter of 7 mm.

10. A method for calculating the penetration depth of a blunt object for a film sample, comprising:
    securing the sample to the top end of a column by extending the edge of the sample along the outside surface of the column,
    lowering a stylus to contact the sample until movement of the stylus is not possible without movement of the sample, recording a vertical height of the stylus, moving the stylus downward until the sample ruptures, and measuring the distance traveled by the stylus from the starting point and the rupture point.

11. The method of claim 10, wherein the stylus is lowered at a constant speed.

12. The method of claim 11, wherein said constant speed is 508.0 mm/min.

13. The method of claim 10, wherein the sample is a glove finger.

14. The method of claim 10, wherein the sample is taken from a glove palm or glove cuff.

15. The method of claim 10, wherein the sample is a uniform thickness film.

16. The method of claim 10, wherein said stylus is longer than said column.

17. A method for testing a film sample, comprising:

securing the sample to the top end of the column by extending the edge of the sample along the outside surface of the column, lowering a stylus to contact the sample until movement of the stylus is not possible without movement of the sample, recording a vertical height of the stylus, moving the stylus downward until the sample ruptures, measuring the distance traveled by the stylus from the starting point and the rupture point, and measuring the force applied by the force applied by the stylus at rupture.

* * * * *